(12) United States Patent
Bonander et al.

(10) Patent No.: US 9,803,254 B2
(45) Date of Patent: Oct. 31, 2017

(54) *SACCHAROMYCES CEREVISAE* STRAINS

(71) Applicant: SCANDINAVIAN TECHNOLOGY GROUP AB, Lund (SE)

(72) Inventors: Nicklas Bonander, Mölndal (SE); Lisbeth Olsson, Västra Frölunda (SE); Elia Tomas-Pejo, Göteborg (SE)

(73) Assignee: Scandinavian Technology Group AB (SE)

( * ) Notice: Subject to any disclaimer, the term of this patent is extended or adjusted under 35 U.S.C. 154(b) by 0 days.

(21) Appl. No.: 15/030,050

(22) PCT Filed: Oct. 15, 2014

(86) PCT No.: PCT/SE2014/051219
§ 371 (c)(1),
(2) Date: Apr. 15, 2016

(87) PCT Pub. No.: WO2015/057148
PCT Pub. Date: Apr. 23, 2015

(65) Prior Publication Data
US 2016/0244851 A1    Aug. 25, 2016

(30) Foreign Application Priority Data

Oct. 16, 2013  (SE) .................................. 1351225
May 6, 2014   (SE) .................................. 1450538

(51) Int. Cl.
| | | |
|---|---|---|
| C12N 1/16 | (2006.01) | |
| C12P 7/10 | (2006.01) | |
| C12N 15/04 | (2006.01) | |
| C12R 1/865 | (2006.01) | |
| C12N 1/18 | (2006.01) | |
| C12N 9/04 | (2006.01) | |
| C12P 19/14 | (2006.01) | |

(52) U.S. Cl.
CPC ............ *C12R 1/865* (2013.01); *C12N 1/16* (2013.01); *C12N 1/18* (2013.01); *C12N 9/0006* (2013.01); *C12N 15/04* (2013.01); *C12P 7/10* (2013.01); *C12P 19/14* (2013.01); *Y02E 50/16* (2013.01); *Y02E 50/17* (2013.01)

(58) Field of Classification Search
None
See application file for complete search history.

(56) References Cited

U.S. PATENT DOCUMENTS

| | | | |
|---|---|---|---|
| 5,693,526 A | 12/1997 | Mondal et al. | |
| 7,531,348 B2 | 5/2009 | Cordero Otero et al. | |
| 8,962,289 B2 * | 2/2015 | Albers ................... | C12P 7/10 435/161 |

FOREIGN PATENT DOCUMENTS

| | | |
|---|---|---|
| WO | WO 2005/121337 A1 | 12/2005 |
| WO | WO 2009/155633 A1 | 12/2009 |
| WO | WO 2012/067571 A1 | 5/2012 |
| WO | WO 2012/067572 A1 | 5/2012 |

OTHER PUBLICATIONS

Knop, Michael; "Evolution of the hemiascomyceteyeasts: on life styles and theimportance of inbreeding" BioEssays, 28, 696-708, 2006.*
Hadfield, C; et al; "G418-resistance as a dominant marker and reporter for in *Saccharomyces cerevisiae*" Current Genetics, 18, 303-313, 1990.*

* cited by examiner

*Primary Examiner* — David Berke-Schlessel
(74) *Attorney, Agent, or Firm* — Condo Roccia Koptiw LLP

(57) ABSTRACT

The present invention relates to a method of preparing a strain of sugar fermenting *Saccharomyces cerevisiae* with capability to ferment xylose, wherein said method comprises different procedural steps. The method comprises mating a first sporulated *Saccharomyces cerevisiae* strain with a second *Saccharomyces cerevisiae* haploid strain. Thereafter, screening for mated cells is performed, growing such mated cells, and verifying that mated cells exhibit basic morphology by microscopic inspection. Thereafter, creation of a mixture of the mated cells is performed, subjecting the mixture to continuous chemostat cultivation and obtaining the sugar fermenting *Saccharomyces cerevisiae* cells with capability to ferment xylose is performed. The invention also comprises strains obtained by said method.

7 Claims, 11 Drawing Sheets

1 2 3 4

1. Taurus04 (haploid, mating type alfa)
2. USM21 is diploid
3. Taurus11 is diploid
4. 1kb DNA ladder (the six bands from bottumn are: 0.5, 0.75, 1, 1.5, 2, 2.5, 3kb)

Birch hydrolysate

Bagasse hydrolysate

Wheat straw hydrolysate at pH 5.5

Fig. 7

Table 1

| Media | Gluc. | Xyl. | TS | HMF | Time for HMF at 0g/L (h) | Furfural | Time for Furfural at 0g/L (h) | Acetate (g/L) | Y EtOH/ TS | Y xylitol/ consumed xyl. | Y glycerol/TS |
|---|---|---|---|---|---|---|---|---|---|---|---|
| wheat straw pH 5.5 | 3,3 | 16,4 | 19,7 | 0,05 | - | 1,4 | 4.0 | 2,8 | 0,49 | 0,02 | 0,02 |
| Birch pH 6 | 2,3 | 16,0 | 18,3 | 0,05 | 11,5 | 0.8 | 9,5 | 4,6 | 0,50 | 0,03 | 0,03 |
| Bagasse pH 5.5 | 2,4 | 7,1 | 9,5 | 0,3 | 11,5 | 2.0 | 10 | 2,8 | 0,52 | 0,00 | 0,06 |

1. TS=total sugar (g/L glucose+ g/L xylose).
2. Y is yield (g/g) of main products in yeast anaerobic fermentation: ethanol, xylitol or glycerol.

Energy grass hydrolysate v1 pH 4

Energy grass hydrolysate v1 pH 5.5

Energy grass hydrolysate v1 pH 6.0

Energy grass v1 pH 5.5 with 17g/L glucose and 23g/L xylose

Wheat straw pH 4.0

Wheat straw, Fed-batch

SSF 10% WIS wheat straw

Fig. 17
Table 2

| Media[3] | Glucose (g/L) | Xylose (g/L) | TS (g/L) | HMF (g/L) | Time for HMF at 0g/L (h) | Fur-fural (g/L) | Time for Furfural at 0g/L (h) | Acet-ate (g/L) | Y[2] EtOH/TS | Y[2] xylitol/ cons. xylose | Y[2] glycerol/TS |
|---|---|---|---|---|---|---|---|---|---|---|---|
| EGV1 pH4 | 2,5 | 17,5 | 20,0 | 0,05 | 4 | 0,4 | 4 | 3,2 | 0,56 | 0,04 | 0,00 |
| EGV1 pH 5.5 | 2,4 | 17,3 | 19,7 | 0,05 | 4 | 0,4 | 4 | 3,4 | 0,51 | 0,03 | 0,01 |
| EGV1 pH 6 | 2,4 | 16,9 | 19,4 | 0,05 | 4 | 0,4 | 4 | 3,0 | 0,53 | 0,02 | 0,01 |
| EGV1 pH5.5 17Glc+23xyl | 16,9 | 22,7 | 39,5 | 0,05 | 4 | 0,4 | 4 | 3,0 | 0,55 | 0,02 | 0,02 |
| EGV1 pH5.5 18Glc+47Xyl | 19,1 | 47,5 | 66,6 | 0,05 | 4 | 0,4 | 4 | 3,0 | 0,51 | 0,01 | 0,02 |
| EGV2 | 9,6 | 85,1 | 94,7 | 0,03 | 2 | 0,3 | 2 | 6,4 | 0,48 | 0,02 | 0,01 |
| Wheat straw pH4 | 26,9 | 25,8 | 52,7 | 0,2 | 19 | 1,4 | 19 | 2,5 | 0,44 | 0,04 | 0,00 |
| Wheat straw pH5.5 Fed-batch 0-48h | 66,1 | 33,8 | 99,9 | 0,1 | 2 | 1,2 | 2 | 2,6 | 0,47 | 0,03 | 0,04 |
| Wheat straw pH5.5 Fed-batch 48-110h | 33,1 | 66,8 | 100,0 | - | - | - | - | 2,6 | 0,50 | 0,03 | 0,00 |
| Wheat straw SSF pH5.5 | 6,0 | 26,9 | 32,8 | 0,3 | 6 | 2,6 | 6 | 4,5 | - | - | - |

1. TS=total sugar (g/L glucose+ g/L xylose).
2. Y is yield (g/g) of main products in yeast anaerobic fermentation: ethanol, xylitol or glycerol.

EGV1 = Energy

SACCHAROMYCES CEREVISAE STRAINS

CROSS REFERENCE TO RELATED APPLICATIONS

This application is the National Stage Entry under 35 U.S.C. §371 of Patent Cooperation Treaty Application No. PCT/SE2014/051219, filed Oct. 15, 2014, which claims the benefit of Swedish Patent Application 1351225-6, filed Oct. 16, 2013, and the benefit of Swedish Patent Application No. 1450538-2, filed May 6, 2014, the contents of which are hereby incorporated by reference herein.

TECHNICAL FIELD OF THE INVENTION

The present invention relates to a method of preparing a strain of sugar fermenting *Saccharomyces cerevisiae* with capability to ferment xylose, and to the use of said prepared strains of the invention for fermentation of sugar containing biomass hydrolysates to ethanol.

BACKGROUND ART

Strains of the genus *Saccharomyces* are used widely in the industry for brewing, distilling, baking and various other applications. *Saccharomyces cerevisiae* is one of the most widely used microorganisms in industrial applications in view of it's ability to convert sugars such as glucose and sucrose to cell mass, and fermenting these sugars to ethanol. Strains of *Saccharomyces cerevisiae* are used in the fuel industry in view of their ability to rapidly convert sugars into ethanol. *Saccharomyces cerevisiae* has a better tolerance towards fermentation inhibitors and ethanol compared to bacteria and other yeasts.

Unlike bacteria and several yeast species, wild-type *Saccharomyces cerevisiae* is not able to use pentoses such as xylose and arabinose as carbon source. The ability of *Saccharomyces cerevisiae* to grow on abundant carbon sources such as side streams and residual material from other processes, such as agricultural residual material from e.g. maize and bagasse, and residual material from e.g. paper manufacture, is of great environmental, but also economical, value. Agricultural residual material comprises a rather large fraction of hemicellulose, which contains many different sugar monomers. For instance, besides glucose, these sugar monomers can include xylose, mannose, galactose, rhamnose and arabinose. Glucose and xylose are the sugar monomers that are present in the largest amount and thus represents an important carbon source for the manufacturing of ethanol using yeasts, providing a huge economic and environmental advantage. The abundance of xylose in mentioned materials and the possibility to use yeasts, such as *Saccharomyces cerevisiae*, to produce ethanol using xylose as carbon source has led to intense research within this field of technology. The conversion of xylose has however sometimes been poor resulting in a poor ethanol production. Further the production of the byproduct xylitol has been rather large.

Genes encoding enzymes giving the ability to use xylose as carbon source have previously been introduced in *Saccharomyces cerevisiae*. EP 1 282 686 discloses recombinant *Saccharomyces cerevisiae* strains having incorporated genes for the enzymes xylose reductase, xylitol dehydrogenase and xylulokinase as well as having been subjected to a specific mutation. Said strains have the ability to ferment lignocellulose raw materials to ethanol. The strain deposited in Ep 1 282 686 is CBS 102679 (TMB3400, Taurus 01) is generally recognised to be efficient in the prior art. The ethanol produced by the strain CBS 102679 has been considered very good compared to other prior art recombinant yeasts, but there is also a production of the undesirable byproduct xylitol. Therefore, there is still a need within the art to provide new strains of *Saccharomyces cerevisiae* having an even better ethanol production, better xylose conversion as well as lower xylitol production. WO2012/067571 and WO2012/067572 disclose *Saccharomyces cerevisiae* strains Taurus03 with deposit number CBS128138, Taurus04 with deposit number CBS 128139, Taurus07 with deposit number CBS128140, Taurus10 with deposit number CBS128141, which all are xylose fermenting yeast strains producing beneficial ethanol yields.

WO2005/121337 discloses methods for producing non-recombinant strains of *Saccharomyces* capable of growing aerobically on xylose at a desired growth rate of at least one generation per 48 hours. In the described method pooling of cells takes place before sporulation of cells The β-lactamase gene is included in at least the strains Taurus04 and Taurus07 as mentioned above. The authorities in the US do not allow the use of *Saccharomyces cerevisiae* strains, which contain the β-lactamase gene, in larger production facilities in view of risk for genetic transfer of the gene to another organism which then potentially can obtain antibiotic resistance.

There is still a need within the technical field to provide robust *Saccharomyces cerevisiae* strains providing high ethanol yields from both 5- and 6-carbon sugars and in addition providing low by-product yields of eg xylitol. *Saccharomyces cerevisiae* strains not having the above mentioned β-lactamase gene in the genome are especially needed.

SUMMARY OF INVENTION

In view of the above, the present invention relates to efficient *Saccharomyces cerevisiae* strains that have been prepared by the method as described below. The strains prepared have reached ethanol yields during fermentation of sugars being close to the theoretical possible in view of the total amount of sugar present in the fermentation medium, eg a biomass hydrolysate.

The present invention relates, in one aspect, to a method of preparing a strain of sugar fermenting *Saccharomyces cerevisiae* with capability to ferment xylose, wherein said method comprises the steps:
   a) sporulating a first strain of *Saccharomyces cerevisiae* for providing at least 20 tetrads of said strain,
   b) mating the first sporulated *Saccharomyces cerevisiae* strain with a second *Saccharomyces cerevisiae* haploid strain by mixing cells of said *Saccharomyces cerevisiae* haploid strain with each tetrad obtained in step a) to provide mated cells on an YPD agar plate,
   c) screening for mated cells on xylose and geneticin agar plates,
   d) growing mated cells from step c) in minimal defined xylose liquid media,
   e) verifying that the mated cells exhibit basic morphology features of budding yeast by microscopic inspection and selecting such mated cells with basic morphological features,
   f) creation of a mixture of the mated cells with basic morphology features in equal amounts from step e),
   g) subjecting the mixture to continuous chemostat cultivation firstly in a microaerobic environment and thereafter in a anaerobic environment using feeding strategy with defined xylose media feed at at least 0.08 h$^{-1}$ in cyclus of feed and disrupted feed in a cyclus time range of a few hours, h) obtaining the sugar fermenting *Saccharomyces cerevisiae* cells with capability to ferment xylose by collecting said cells from the chemostat reactor.

The present invention relates, in another aspect, to a strain of *Saccharomyces cerevisiae* obtainable by the method as described above. The present invention relates, in yet another aspect, to a strain that is Taurus 11 having deposition number CBS136254, deposited on Oct. 1, 2013, at Centraalbureau voor Schimmelcultures, Uppsalalaan 8, 3584 CT Utrecht, the Netherlands.

The present invention relates, in yet another aspect, to the use of a strain of *Saccharomyces cerevisiae* obtainable as described above, for fermentation of sugar containing hydrolysates or biomass to ethanol.

BRIEF DESCRIPTION OF DRAWINGS

FIG. 7 shows Table 1. Anaerobic fermentation experiments of glucose and xylose with a strain of the invention. Listed values in g/L are the sugars glucose and xylose, and the inhibitors hydroxymethylfurfural (HMF) and furfural. Also shown is the yield of ethanol from total sugar concentrations and the yield of main by-products glycerol and xylitol.

FIG. 17 shows table 2. Anaerobic fermentation experiments of glucose and xylose with a strain of the invention. Listed values for the sugars glucose and xylose, and the inhibitors hydroxymethylfurfural (HMF) and furfural are given in g/L. Also shown is the yield of ethanol from total sugar concentrations and the yield of main by-products glycerol and xylitol.

DETAILED DESCRIPTION OF THE INVENTION

Figure 1:
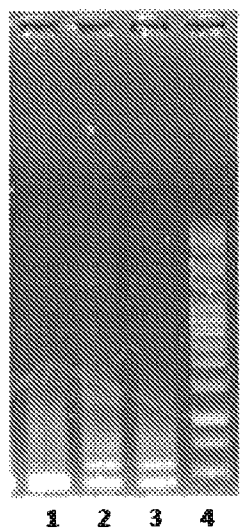
FIG. 1. Agarose gel DNA electrophoresis of A and alfa locus amplified from genomic DNA. After migration of the PCR fragments at 100 v 30 min the gel stained with GelRed and the dye-DNA complex was excited with UV light and a detected with digital camera. The agarose gel electrophoreses shows evolved Taurus 04 (haploid, mating type alfa), USM21 (diploid) and Taurus11 (diploid). In Lane 4 a DNA size marker is shown, from bottom the mass of six bands are (in kilo base pair): 0.5, 0.75, 1, 1.5, 2, 2.5, 3 kb.

In an embodiment of the invention, there is provided a method of preparing a strain of sugar fermenting *Saccharomyces cerevisiae* with capability to ferment xylose, wherein said method comprises different important procedural steps. *Saccharomyces cerevisiae* strains ferments glucose naturally and has by means of the present invention been prepared to ferment xylose as well at a high rate. Other sugars are also fermented with a strain according to the present invention, e.g. glucose, and galactose.

The method of the present invention comprises the following steps.

Step a) concerns sporulating a first strain of *Saccharomyces cerevisiae* for providing at least 20 tetrads of said strain, wherein this step proceeds for at least 1 week at at least room temperature. A temperature in the range of 20-30° C. provides the desired results. Sporulating *Saccaromyces cerevisiae* is performed as in its ordinary sense within the technical field.

Step b) concerns mating the first sporulated *Saccharomyces cerevisiae* strain with a second *Saccharomyces cerevisiae* haploid strain by mixing cells of said *Saccharomyces cerevisiae* haploid strain with each tetrad obtained in step a) to provide mated cells on an YPD agar plate, wherein this step proceeds for at least 1 week at at least room temperature. A temperature in the range of 20-30° C. provides the desired mating results.

Step c) concerns screening for mated cells on xylose and geneticin agar plates, wherein the xylose and geneticin agar plates comprises 50-150 µg/ml geneticin, preferably about 100 µg/ml geneticin, and 15-25 g/L xylose, preferably 20 g/L xylose. In an embodiment of the invention, the first strain of *Saccharomyces cerevisiae* is USM21 (CBS102678) and the second strain of *Saccharomyces cerevisiae* is Taurus04. Taurus04 can grow on xylose, but it is not resistant to the geneticin antibiotic, while USM21 can not grow on xylose but is resistant to geneticin. Therefore, it is only the mated cells that are able to grow on the geneticin+xylose plate. The resistance of USM21 is not from a transformation of the geneticin resistance gene. The resistance of USM21 to grow on the geneticin is gained by some cellular mechanism.

Step d) concerns growing mated cells from step c) in minimal defined xylose liquid media, wherein the minimal defined xylose liquid media is for example in the range 15-25 g/L xylose, preferably about 20 g/L xylose, defined media liquid culture. This step is performed in order to quantitatively increase the amount of cells.

Step e) concerns verifying that the mated cells exhibit basic morphology features of budding yeast by microscopic inspection and selecting such mated cells with basic morphological features. To a person skilled in the art it is clear which type of mated cells, exhibiting basic morphological features of budding yeast, are and can be chosen from the microscopic inspection.

Step f) concerns creation of a mixture of the mated cells with basic morphology in equal amounts from step e), wherein the equal amounts of the basic, mated cells in this step is typically in the range of $1 \times 10^6$ cells/ml-$1 \times 10^8$ cells/ml, especially about $0.5 \times 10^7$-$2 \times 10^7$ cells/ml.

Step g) concerns subjecting the mixture to continuous chemostat cultivation firstly in a microaerobic environment and thereafter in a anaerobic environment using feeding strategy with defined xylose media feed at at least 0.08 h$^1$, preferably at least 0.10 h$^{-1}$, and more preferably at least 0.12 h$^{-1}$, in cyclus of feed and disrupted feed in a cyclus time range of a few hours, eg 4-8 hours, eg 5, 6, or 7 hours. The dilution rate (h$^{-1}$) can be adjusted in order to obtain cells with correct characteristics.

Step h) concerns obtaining the sugar fermenting *Saccharomyces cerevisiae* cells with capability to ferment xylose by collecting said cells from the chemostat reactor. The cells collected ferment xylose efficiently in addition to sugars as it ferments normally, i.e. glucose and sucrose etc.

In an embodiment of the invention the second *Saccharomyces cerevisiae* haploid strain is obtained from the deposited yeast strains Taurus03 with deposit number CBS128138, deposited on Oct. 26, 2010, Taurus04 with deposit number CBS 128139, deposited on Oct. 26, 2010, Taurus07 with deposit number CBS128140, deposited on Oct. 26, 2010, Taurus10 with deposit number CBS128141, deposited on Nov. 2, 2010, at Centraalbureau voor Schimmelcultures, Uppsalalaan 8, 3584 CT Utrecht, the Netherlands. The above strains as used in the method according to the invention have the β-lactamase gene removed, are haploid and are evolutionary engineered for increased xylose uptake rates using chemostat cultivation and repetitive batch with both defined xylose media and ligno cellulose.

In an embodiment of the invention, the first strain of *Saccharomyces cerevisiae* for providing at least 20 tetrads of said strain is *Saccharomyces cerevisiae* USM21 with deposition number CBS102678, deposited at Centraalbureau voor Schimmelcultures (CBS), Delft, the Netherlands. In another embodiment of the invention, a strain of *Saccharomyces cerevisiae* is obtainable by the method as described above.

In an embodiment of the invention, an exemplary strain and obtained according to the method as described above is Taurus 11 having deposition number CBS136254, deposited on Oct. 1, 2013, at Centraalbureau voor Schimmelcultures, Uppsalalaan 8, 3584 CT Utrecht, the Netherlands.

In another embodiment, the present invention relates to the use of a strain of *Saccharomyces cerevisiae* prepared according to above described method, for fermentation of sugar containing hydrolysates to ethanol, wherein said sugar is chosen from the group sucrose, glucose, xylose, fructose, mannose, arabinose and galactose or any combination thereof. The hydrolysate may contain one or more of above mentioned sugars and other sugars not specifically mentioned here. The pH of said sugar containing hydrolysates is preferably in the range of 4-6, but fermentation of a hydrolysate could also function at pH below or above the range 4-6. In an embodiment of the invention the sugar containing hydrolysate is a lignocellulose hydrolysate. Hydrolysates are typically liquid. The strain according to the invention can also ferment hydrolysed solid materials such as pretreated biomass or any other sugar containing solid material.

There are many different sugar containing hydrolysates and lignocellulose hydrolysates available within the technical field and any such hydrolysates may be used together with the *Saccharomyces cerevisiae* strain as prepared according to the method of the present invention. The lignocellulose hydrolysates may be chosen from any agricultural or forest residues such as energy crops and whole crop. Examples of such lignocellulose hydrolysates are energy grass hydrolysates, bagasse hydrolysates, straw hydrolysates, eg wheat straw hydrolysates, corn cob hydrolysates, sugar cane hydrolysates, hardwood hydrolysates, softwood hydrolysates, eg birch hydrolysates, corn stover hydrolysates and any combination thereof. The above list is non-exhaustive.

The amount of ethanol produced by a strain of the invention is in the range 35-51 g ethanol/100 g consumed xylose and glucose, 1-3 g xylitol/100 g consumed xylose and 1-3 g glycerol/100 g consumed xylose and glucose.

The fermentation of sugar containing hydrolysates with a strain according to the invention can take place in a batch fermentation, a fed-batch fermentation, a continuous fermentation, in a simultaneous saccharification and fermentation (SSF) process, in a simultaneous saccharification and co-fermentation (SSCF) process or a prehydrolysis and simultaneous saccharification and fermentation (PSSF) process.

In an embodiment of the invention the use of a strain, as prepared, when fermenting a sugar containing hydrolysate leads to high ethanol yields. It has been shown that the strain of the invention can handle both high and low concentrations of both xylose and glucose.

In another embodiment of the invention, the use of a strain as prepared, when fermenting a sugar containing hydrolysate leads to high ethanol yields even in the presence of inhibitors such as from furfural, HMF, formic acid, leuvulinic acid, acetic acid and phenolics.

Thus, according to the present invention, robust *Saccharomyces cerevisiae* strains have been obtained providing high ethanol yields, low by-product yields such as xylitol even in the presence of high concentrations of inhibitors. Thus, a strain that ferments xylose, in addition to other sugars present, in ligno cellulose material at a yield of 35-51 gram ethanol per 100 gram consumed xylose and glucose has been provided. The strain according to the present invention has a high xylose consumption rate that is close to that of glucose consumption rate, which is highly desirable. The strain according to the present invention can propagate in a defined xylose media at a rate of mu=0.35 h$^{-1}$ (+−0.02).

The strain of the invention is free from the β-lactamase gene, an antibiotic resistance gene often introduced upon genetic engineering of the yeast for obtaining new traits.

It has been shown clearly that a strain according to the present invention can perform well in anaerobic fermentation of xylose in three different types of hydrolysates (bagasse, birch and wheat straw).

Figure 4:
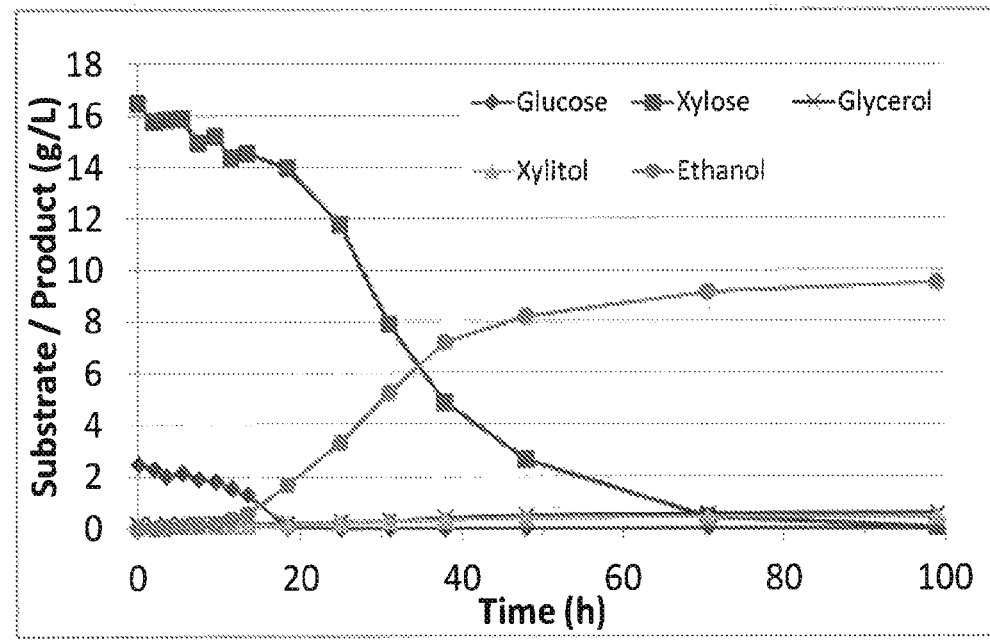
FIG. 4. Anaerobic fermentation of glucose and xylose with a strain of the invention in birch hydrolysate at pH 6. Main glucose fermentation phase starts when the inhibtors HMF (0.05 g/L), furfural (0.8 g/L) have been metabolised at 11.5 h, the media also contains 4.6 g/L acetate. At time 0 h xylose is present at about 16 g/L and glucose at about 2 g/L. At about 60 h the sugars have almost been consumed and the ethanol production has occurred at high yields (table 1), and there is only a minute formation of the by-products xylitol and glycerol. The strain reaches high ethanol yields in the presence of inhibitors.
Figure 5:
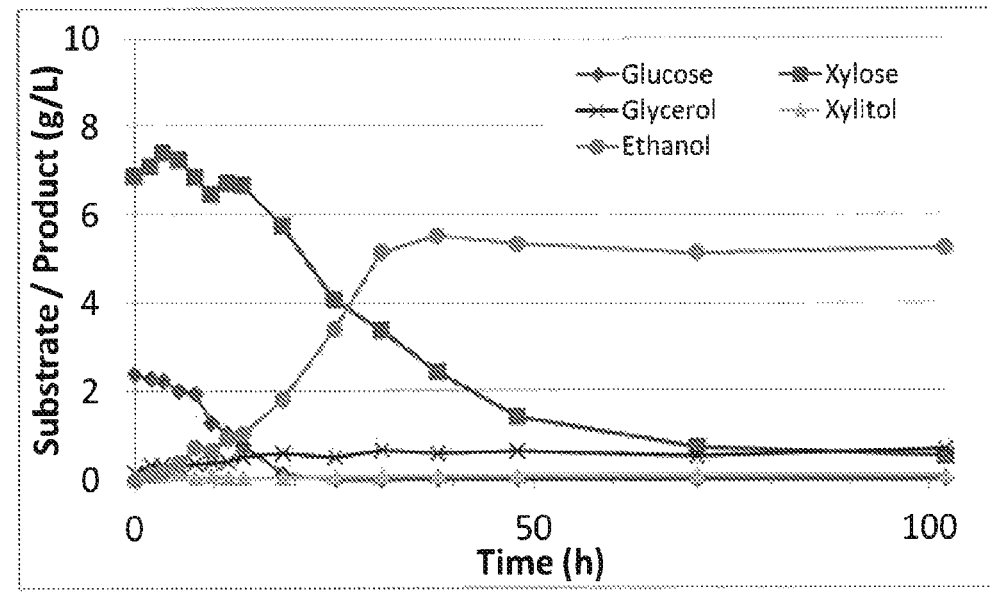
FIG. 5. Anaerobic fermentation of glucose and xylose with a strain of the invention in bagasse hydrolysate at pH 5.5. Main glucose fermentation phase starts when the inhibtors HMF (0.3 g/L), furfural (2.0 g/L) have been metabolised at 10 h, the media also contains 2.8 g/L acetate. At time 0 h xylose is present at about 7.1 g/L and glucose at about 2.4 g/L. At about 50 h the sugars have almost been consumed and the ethanol production has occurred at high yields (table 1), and there is only a minute formation of the by-products xylitol and glycerol. The strain reaches high ethanol yields in the presence of high concentrations of inhibitors.
Figure 6:
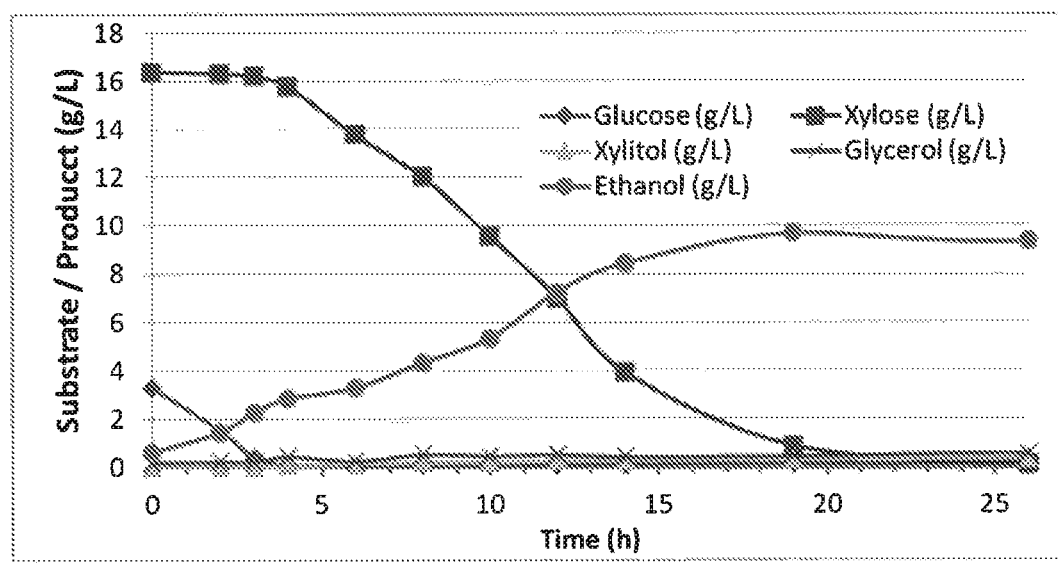
FIG. 6. Anaerobic fermentation of glucose and xylose with a strain of the invention in wheat straw hydrolysate at pH 5.5. Main glucose fermentation phase starts when the inhibtors HMF (0.05 g/L), furfural (1.4 g/L) have been metabolised at 4 h, the media also contains 2.8 g/L acetate. At time 0 h xylose is present at about 16.4 g/L and glucose at about 3.3 g/L. At about 19 h the sugars have almost been consumed and the ethanol production has occurred at high yields (table 1), and there is only a minute formation of the by-products xylitol and glycerol. The strain reaches high ethanol yields in the presence of high concentrations of inhibitors.
Figure 8:
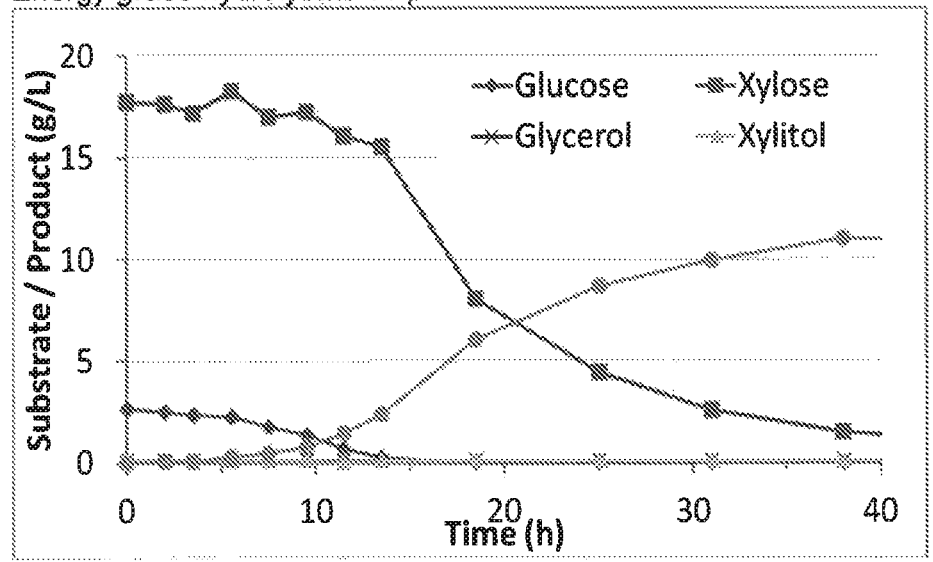
FIG. 8. Anaerobic fermentation of glucose and xylose with a strain of the invention in energy grass hydrolysate version 1 at pH 4.0. Main glucose fermentation phase starts when the inhibitors HMF (0.05 g/L), furfural (0.4 g/L) have been metabolised at 4 h, the media also contains 3.2 g/L acetate. At time 0 h xylose is present at about 17.7 g/L and glucose at about 3.6 g/L. At about 38 h the sugars have almost been consumed and the ethanol production occured at high yields (table 2) and there is only a minute formation of the by-products xylitol and glycerol. The strain reaches high ethanol yields in the presence of inhibitors. Ethanol yield (g/g) is the amount of ethanol produced (g) from consumed sugar (g) (ethanol, xylitol or glycerol) in yeast anaerobic fermentation.
Figure 9:
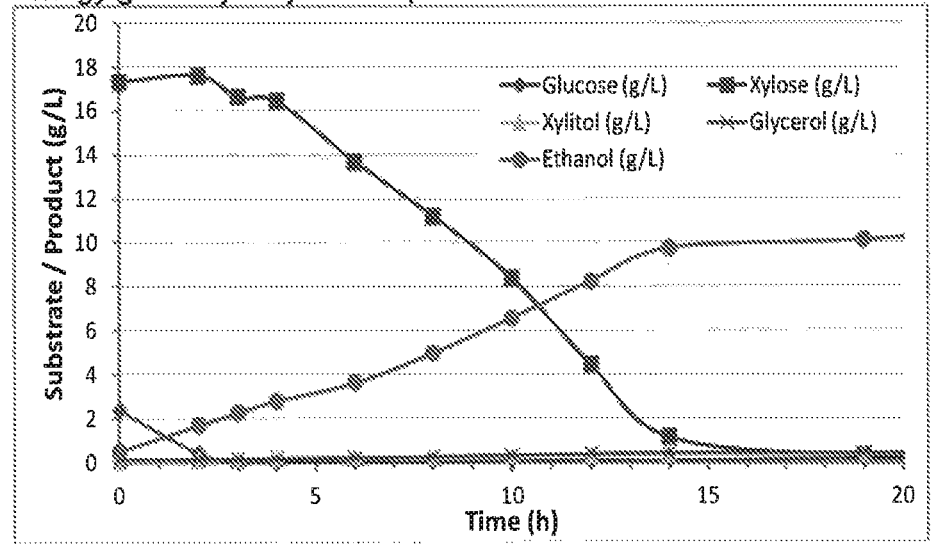
FIG. 9. Anaerobic fermentation of glucose and xylose with a strain of the invention in energy grass hydrolysate version 1 at pH 5.5. Main glucose fermentation phase starts when the inhibitors HMF (0.05 g/L), furfural (0.4 g/L) have been metabolised at 4 h, the media also contains 3.4 g/L acetate. At time 0 h xylose is present at about 17.5 g/L and glucose at about 2.4 g/L. At about 14 h the sugars have almost been consumed and the ethanol production has occurred at high yields (table 2), and there is only a minute formation of the by-products xylitol and glycerol. The strain reaches high ethanol yields in the presence of inhibitors.
Figure 10:
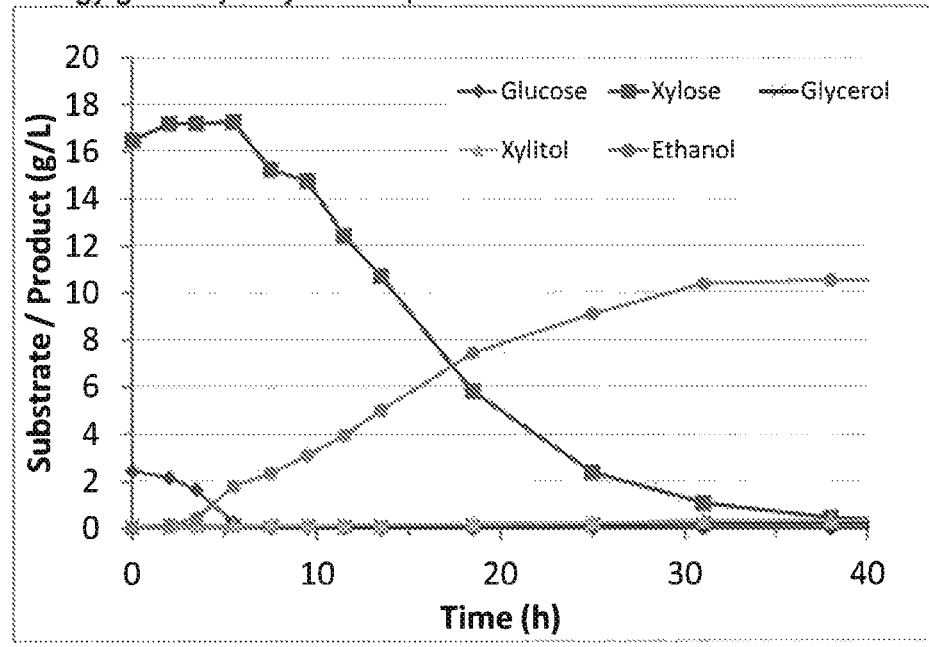
FIG. 10. Anaerobic fermentation of glucose and xylose with a strain of the invention in energy grass hydrolysate version 1 at pH 6.0. Main glucose fermentation phase starts when the inhibitors HMF (0.05 g/L), furfural (0.4 g/L) have been metabolised at 4 h, the media also contains 3.0 g/L acetate. At time 0 h xylose is present at about 17.2 g/L and glucose at about 2.4 g/L. At about 35 h the sugars have almost been consumed and the ethanol production has occurred at high yields (table 2), and there is only a minute formation of the by-products xylitol and glycerol. The strain reaches high ethanol yields in the presence of inhibitors.
Figure 11:
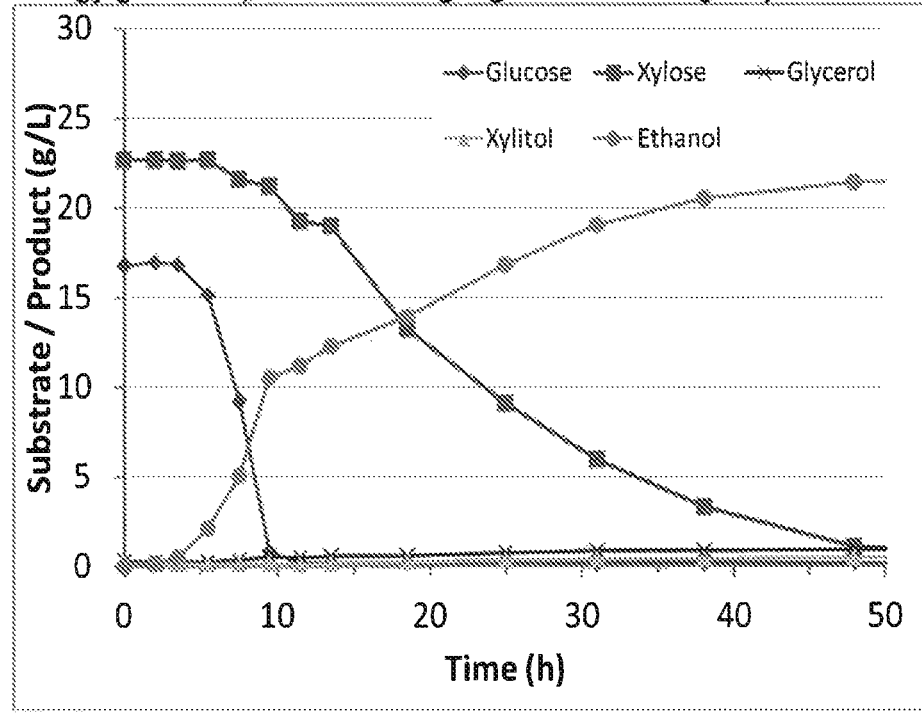
FIG. 11. Anaerobic fermentation of glucose and xylose with a strain of the invention in energy grass hydrolysate version 1 at pH 5.5 with 17 g/L glucose and 23 g/L xylose. Main glucose fermentation phase starts when the inhibitors HMF (0.05 g/L), furfural (0.4 g/L) have been metabolised at 4 h, the media also contains 3.0 g/L acetate. At time 0 h xylose is present at about 22.7 g/L and glucose at about 16.9 g/L. At about 45 h the sugars have almost been consumed and the ethanol production has occurred at high yields (table 2), and there is only a minute formation of the by-products xylitol and glycerol. The strain reaches high ethanol yields in the presence of inhibitors.
Figure 12:
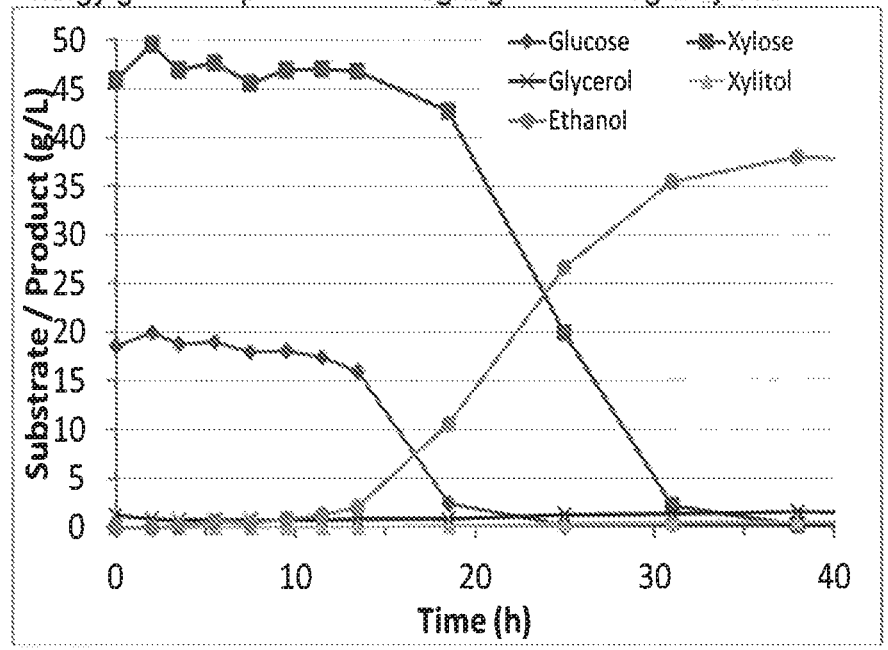
FIG. 12. Anaerobic fermentation of glucose and xylose with a strain of the invention in energy grass hydrolysate version 1 at pH 5.5 with 18 g/L glucose+47 g/L xylose. The inhibitors HMF (0.05 g/L) and furfural (0.4 g/L) are present and have been metabolised at 4 h, the media also contains 3.0 g/L acetate. The glucose and xylose fermentation starts at 15 h. At time 0 h xylose is present at about 47.0 g/L and glucose at about 18.5 g/L. At about 30 h the sugars have almost been consumed and the ethanol production has occurred at high yields (table 2), and there is only a minute formation of the by-products xylitol and glycerol. The strain reaches high ethanol yields in the presence of inhibitors.
Figure 13:
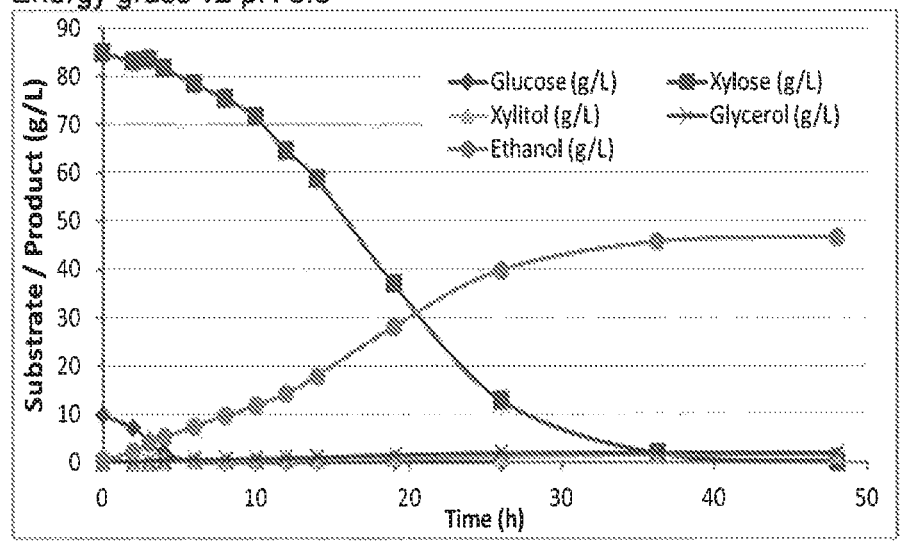
FIG. 13. Anaerobic fermentation of glucose and xylose with a strain of the invention in energy grass hydrolysate version 2 at pH 5.5. The inhibitors HMF (0.03 g/L) and furfural (0.25 g/L) are present and have been metabolised at 2 h, the media also contains 6.5 g/L acetate. The glucose and xylose fermentation starts at 2 h. At time 0 h xylose is present at about 85.0 g/L and glucose at about 9.6 g/L. At about 30 h the sugars have almost been consumed and the ethanol production has occurred at high yieds (table 2), and there is only a minute formation of the by-products xylitol and glycerol. The strain reaches high ethanol yields in the presence of inhibitors.
Figure 14:
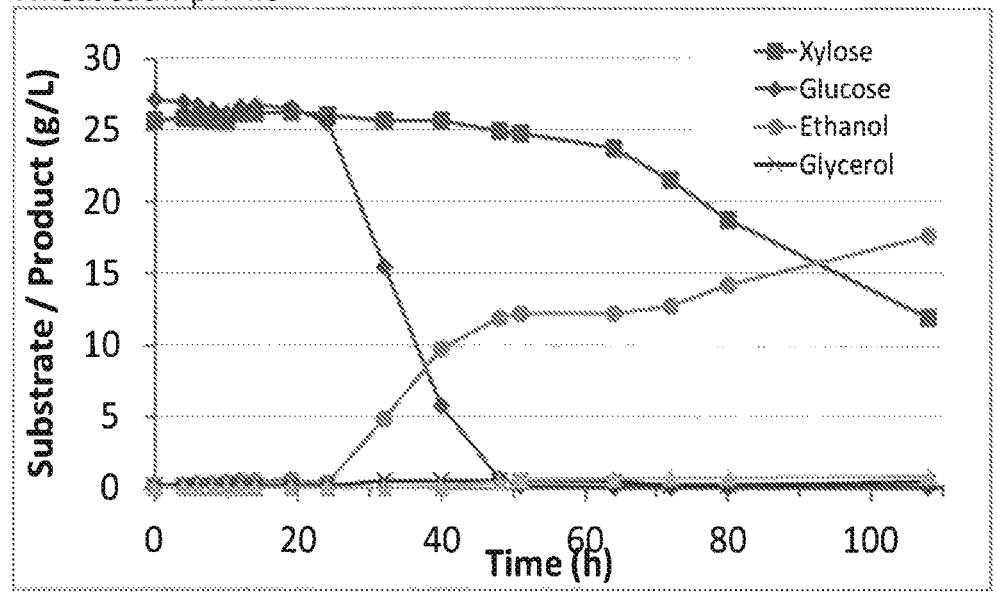
FIG. 14. Anaerobic fermentation of glucose and xylose with a strain of the invention in wheat straw at pH 4.0. The inhibitors HMF (0.17 g/L) and furfural (1.4 g/L) are present and have been metabolised at 19 h, the media also contains 2.5 g/L acetate. The glucose and xylose fermentation starts at 20 h. At time 0 h xylose is present at about 25.8 g/L and glucose at about 27 g/L. At about 100 h the ethanol production has occurred at high yields (table 2), and there is only a minute formation of the by-products xylitol and glycerol. The strain reaches high ethanol yields in the presence of high concentrations of inhibitors.
Figure 15:
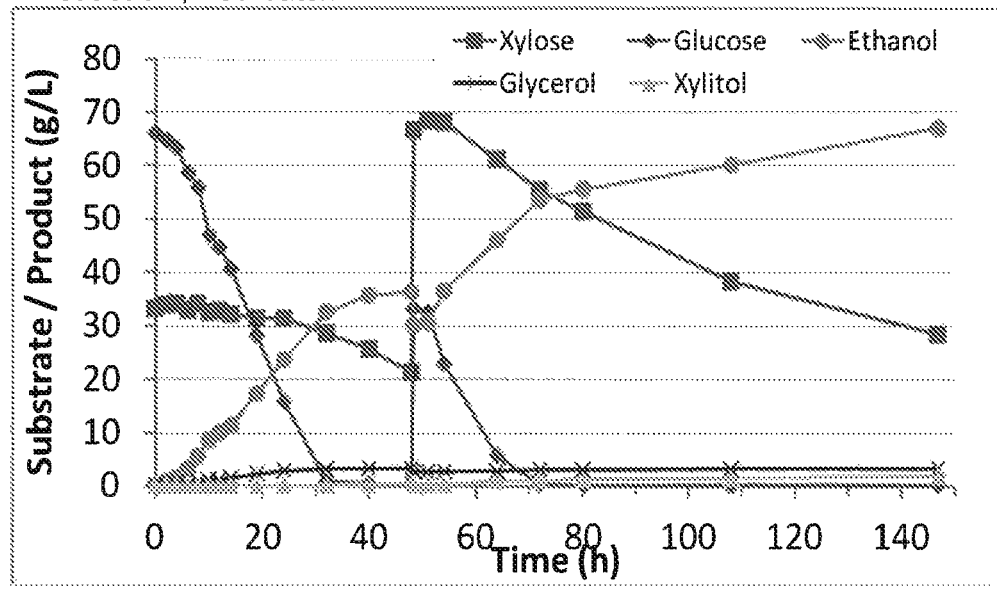
FIG. 15. Anaerobic fed-batch fermentation of glucose and xylose with a strain of the invention in wheat straw (fed-batch) at pH 5.5. The inhibitors HMF (0.13 g/L) and furfural (1.2 g/L) are present and have been metabolised at 2 h, the media also contains 2.6 g/L acetate. The glucose and xylose fermentation starts at 2 h. At time 0 h xylose is present at about 33 g/L and glucose at about 66 g/L. At 48 h more sugars are added to about 67 g/L xylose and 33 g/L glucose. At 147 h, the ethanol concentration reached is high (about 67 g/l) and there is only a minute formation of the by-products xylitol and glycerol. The strain reaches high ethanol yields (table 2) in the presence of inhibitors.
Figure 16:
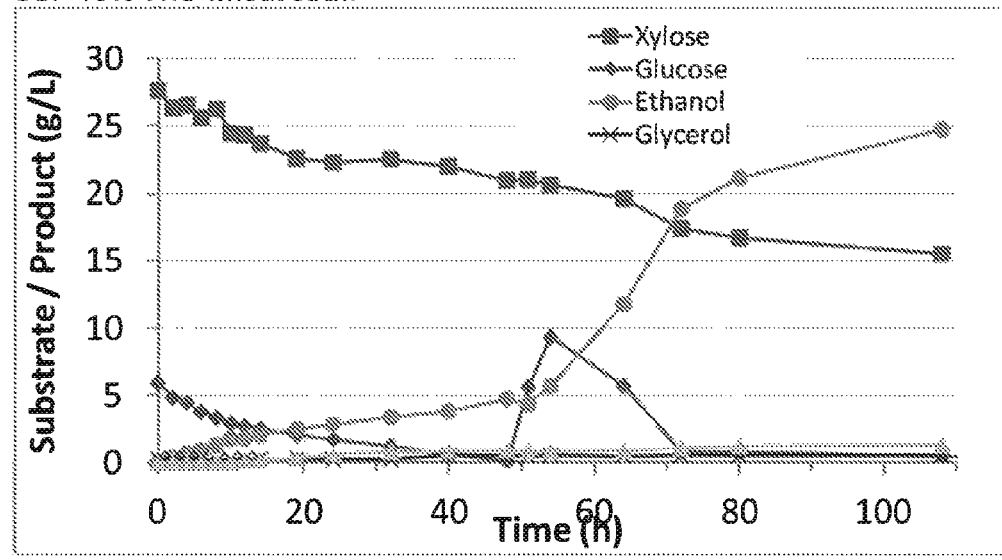
FIG. 16. Anaerobic SSF fermentation of glucose and xylose with a strain of the invention in wheat straw at pH 5.5. The inhibitors HMF (0.3 g/L) and furfural (2.6 g/L) are present and have been metabolised at 6 h, the media also contains 4.5 g/L acetate. The glucose and xylose fermentation starts at 4 h. At time 0 h 10% WIS from pre-treated wheat straw is added, xylose is present at about 27.6 g/L and glucose at about 6 g/L. At 48 h 10 FPU/g WIS of cellulose degrading enzyme mixture is added. At 108 h the ethanol production has occurred at high yields (table 2), and there is only a minute formation of the by-products xylitol and glycerol. The strain reaches high ethanol yields in the presence of high concentrations of inhibitors. SSF=Simultaneous Saccharification and Fermentation

The strain of the invention converts only 1-3% of the consumed xylose into xylitol, see FIGS. 4, 5, and 6.

In addition, a strain according to the present invention is able to ferment >98.5% of available xylose with residual xylose being <0.23 g/L at the end of the fermentation.

All technical terms used in the present application have the meaning as is commonly understood by the skilled man.

The strains of the invention may be prepared from industrial yeast strains as well as laboratory yeast strains even though industrial yeast strains are preferred. An industrial strain is less well defined than the laboratory strains since it has several copies of each chromosome. Thus, manipulating industrial strains, as have been performed according to the present invention, is a larger challenge.

EXPERIMENTAL

Experiment 1

Method description for constructing strain Taurus 11, CBS 136254. Strain sporulation of USM21 (CBS102678) and mating with evolved haploid xylose fermenting strain (CBS128139).

Day 1: Yeast strain USM21 (CBS102678) was streaked onto an YPD agar plate. Yeast strain evolved for xylose fermentation is haploid (hereafter referred to as strain evolved) was streaked on to 20 g/L xylose agar plate and plates incubated at 30° C. for 4 days.

Day 5: USM21 cells was transferred onto a 2% KAc agar plate, and left at 30° C. 4 days, and room-temperature for 3 days. The strain had by then sporulated and individual spores were digested from each other by treatment with 1 mg/ml Lyticase in 10 mM Tris pH 7.5 with 1 mM EDTA for 40 min at 30° C. Individual spores were moved using a dissecting instrument onto a YPD plate and mixed with 1 to several cells of strain evolved. More than 20 such mixes were made. 4 spores from USM21 were also placed on the YPD plate without cells from evolved xylose strain. Plate was incubated at 30° C. for 5 days.

Day 10: Colonies appeared where the mixture of USM21 and evolved xylose strain had been placed, these potentially containing newly mated cells. There were also colonies on the places where only dissected USM21 spores had been placed. Both these types of colonies where picked as well as separate colonies from a xylose agar plate with the evolved strain and grown over-night in liquid YPD media then getting $OD_{600}$=2-5. Equal amounts of cells with mated USM21+evolved strain cultures were mixed and the OD set to 0.1, 0.01 and 0.001 by dilution into water. Then 50 µl of the different OD mixtures were placed onto a xylose-geneticin plate. On the same plate corresponding drops of the single original strains (USM21 and evolved strain) were also placed. The plate was incubated at 30° C. for 5 days.

Day 15: Colonies only appeared in the drop where the OD=0.1 with the mated USM21 and evolved xylose strain cell drop was placed. There was no growth of the cells with only newly dissected USM21 cells or evolved strain added. A few dozen individual colonies where picked of the strain crosses using the dissecting instrument onto a YPD plate with 20 g/L glucose. The YPD plates with the crossed strains were then incubated for 4 days at 30° C.

Day 19: A few dozen colonies were then inspected in the microscope, and only those cells were used that were from colonies that contained cell types that looked like typical budding yeast (like a small and a large egg together). 20 different colonies were grown in individual vials overnight with 15 m 120 g/L glucose minimal media in each. A mixture of cells was created adding an equal amount of cells to make the final OD=2.0 in 10 ml, corresponding to $1\times10^8$ cells. This mixture was then grown aerobically on xylose for 2 weeks in a volume of 100 ml in a shake flask at 130 rpm at 30° C., followed by 2 weeks of semi aerobic growth in a chemostat cultivation in a stirred shake flask at 300 rpm, with defined media 15 g/L xylose feed into the reactor, at a dilution of mu=0.05 $h^{-1}$ with pH4.5-5.5 at 25-30° C.

Figure 2:
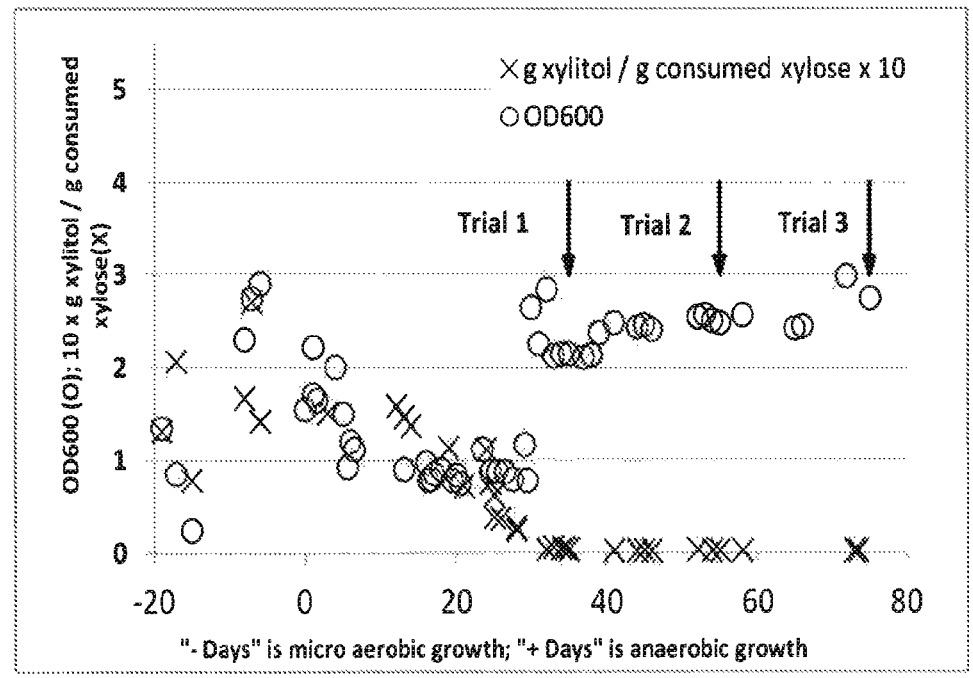
FIG. 2. Evolutionary engineering in chemostat cultivation for selection of a reduced xylitol production and increased xylose uptake. The chemostat cultivation was fed with defined xylose media, where the pump was timed for being on for a few hours and off for a few hours, the average dilution rate was 0.12 h$^{-1}$. The xylitol formation from consumed xylose (X) decreased rapidly after about 30 days, after this time an increased xylose uptake rate was also observed with a concomitant OD increase (O). After these events are arrows indicating where cells were withdrawn for anaerobic fermentation experiments.
Figure 3:
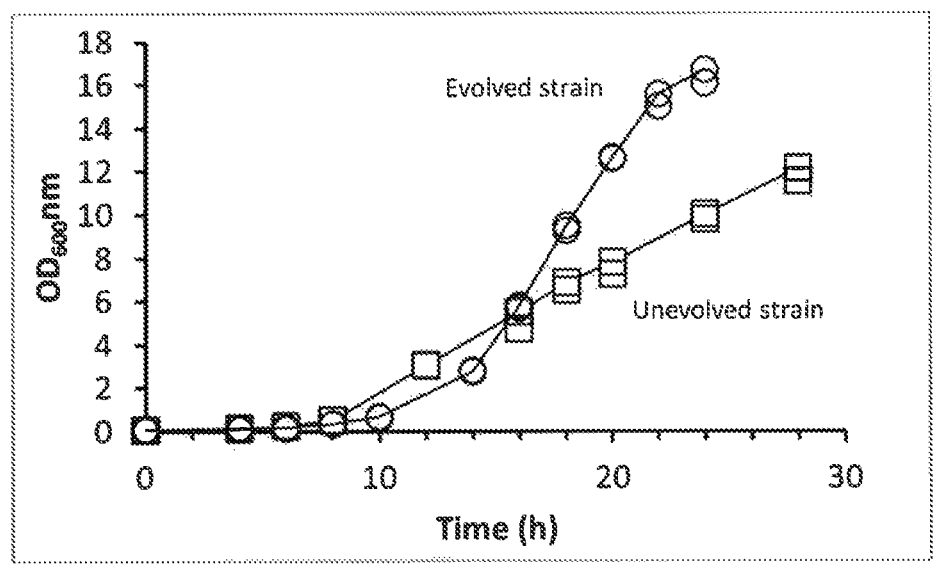
FIG. 3. Growth of unevolved strain and evolved strain in 20 g/L xylose defined media, the cell density was monitored at 600 nm in a separate cuvette. OD$_{600}$ at 0 h was set to 0.05. The evolved cells grow exponentially on xylose media at a rate of mu>0.3 h$^{-1}$.

Day47: The cells in the micro aerobic chemostat were then grown anaerobically for 2 months using 15 g/L xylose defined media, with feed rate of mu=0.12 $h^{-1}$, but with the pump turned off for 6 h then on for 6 h. The pH and temperature were maintained at pH5 and 33° C., respectively. After 1 month, the xylitol yield from consumed xylose was decreasing, and a set of fermentation experiments were performed when xylitol yield was <0.03 g per gram consumed xylose, see FIG. 2. Anaerobic fermentation using lignocellulose material is from the cells taken from the chemostat bioreactor.

Experiment 2

Hydrolysates (pH): Birch hydrolysate pH 6.0; Bagasse hydrolysate pH 5.5; wheat straw hydrolysate pH 5.5, energy grass (version 1) pH 4, energy grass (version 1) pH 5.5, energy grass (version 1) pH 6.0, energy grass (version 1) pH 5.5 with 17 g/L glucose and 23 g/L xylose, energy grass (version 1) pH 5.5 with 17 g/L glucose and 47 g/L xylose, energy grass (version 2) pH 5.5, wheat straw pH 4.0, wheat straw, fed-batch, SSF 10% WIS wheat straw. All hydrolysates were fermented anaerobically with 10 g/L yeast extract added. Description of making agar plates, exemplified with a 2% xylose agar plate (0.5 L): Two separate flasks were autoclaved, 0.25 L with 15 g xylose and 0.25 L with 2.5 g $(NH4)_2SO_4$, 1.5 g $KH_2PO_4$, 0.25 g $MgSO_4$, 0.85 g Yeast nitrogen base and 10 g Agar. A stirrbar was included into one of the flask. After autoclavation, the flasks were set to cool at room-temperature for 10 min, the solutions were mixed in laf bench, stirred for 5 min, the plates were poured with 25 ml media into each 90 mm diameter plate, the plates were left to solidify for 1 h. The plates were stored at 4° C. for up to 3 months. Content description of plates used, following the same procedure as in the 2% xylose agar plate description, and autoclaving sugars separate. YPD agar plate: 20 g/L glucose, 20 g/L Bactopeptone, 10 g/L yeast extract, 20 g/L agar; 2% KAc agar plate: 20 g/L KAc, 20 g/L agar; 2% xylose agar plate: 20 g/L xylose, 1.3 g/L YNB, 5 g/L $(NH4)_2SO_4$, 3 g/L $KH_2PO_4$, 0.2 g/L $MgSO_4\times7H_2O$, 20 g/L agar.

Minimal medium with 15 g/L xylose (1 L): Autoclave in 2 flask separately, 1 flask with 0.5 L $H_2O$ mixed with 15 g xylose, 1 flask with 5 g $(NH4)_2SO_4$, 3 g $KH_2PO_4$, 0.5 g $MgSO_4$. After autoclavation, the solutions were mixed and left to cool for 10 min and then adding 2 ml trace elements solution and 1 ml vitamin solution (Verdyun et al. Journal of Biotechnology, 23(3):303-314, 1992).

Method Description for Anaerobic Fermentation

Day 1: 1000 yeast cells were taken from the chemostat into 70 ml 40 g/L xylose+10 g/L glucose and grown 20 h at 130 rpm and 30° C.

Day 2: After 20 h and when $OD_{600}$=1-3, 30 ml of filtered lignocellulose material (Treatment of ligno cellulose liquid) was added to the culture. The culture was left for 16 h at 130 rpm and 30° C.

Day 3: The cells in the shake flaks were transferred into pre-weighted bottles, and spun at 4000×g for 5 min. After the centrifugation the media was poured of and the remaining 1-2 ml of the residual liquid was removed with a micro-pipette. The bottle with the cell pellet was weighed, and the difference between empty and pellet containing centrifuge tube gave an estimate of the cell amount obtained.

Then 0.6 g wet cells were added to a volume of 50 ml into a 150 ml anaerobic flask with an airlock. The culture was incubated at 30° C. at 130 rpm for up to 100 hours. Samples were taken every second hour the first 16 hours, followed by 2 samples every 5 hour and then every 8-16 h for a total time of 100 hours. The sample was taken by suction out of the anaerobic chamber without opening up the airlock. The airlock glass cylinder was filled with 5 ml 30% glycerol solution during the fermentation.

Treatment of Ligno Cellulose Liquid.

The pH was set to a particular value pH 4, 5.5 or 6 using base addition. Then the solution was filtered using suction through 0.2 um nylon filter. The 45 ml culture of the ligno cellulose material was mixed with 5 ml 100 g/L yeast extract.

Sample Collection and Analysis:

Samples were collected through-out the fermentations, each 0.5-1 ml liquid of sample was filtered through a 0.2 um nylon filter and then the solution was stored at −20° C. until collecting several samples for the HPLC analysis. In order to analyze samples, these were thawed at room temperature for 30 min, and 0.2 ml sample was then mixed with 0.4 ml 5 mM $H_2SO_4$, before loading onto HPLC column. Analysis of sugars and metabolites were performed using a HPLC system (Ultimate 3000, Dionex, Sunnyvale, US). Glucose, xylose, ethanol, xylitol, glycerol, acetic acid, HMF and furfural were separated using an "RESEX ROA-Organic Acids H+(Phenomenex)" column (Bio-Rad Laboratories, München, Germany) with 5 mM $H_2SO_4$ as eluent. The column was operated at 80° C. and at a flow rate of 0.8 mL $min^{-1}$. Ethanol, xylitol, glycerol and acetic acid were detected with a refractive index detector Shodex RI-101 (Showa Denko, New York, N.Y.) while HMF and furfural were detected using an UV detector at 210 nm (Dionex, Sunnyvale, US).C

The invention claimed is:

1. A method of preparing a strain of sugar fermenting *Saccharomyces cerevisiae* with capability to ferment xylose, wherein said method comprises:
    sporulating a first strain of *Saccharomyces cerevisiae* for providing at least 20 tetrads of said strain,
    mating the first sporulated *Saccharomyces cerevisiae* strain with a second *Saccharomyces cerevisiae* haploid strain by mixing cells of said *Saccharomyces cerevisiae* haploid strain with each tetrad to provide mated cells on an YPD agar plate,
    screening for the mated cells on xylose and geneticin agar plates,
    growing the mated cells in minimal defined xylose liquid media,
    verifying that the mated cells exhibit basic morphology features of budding yeast by microscopic inspection and selecting such mated cells with basic morphological features,
    creating a mixture of the mated cells with basic morphology features,
    subjecting the mixture to continuous chemostat cultivation firstly in a microaerobic environment and thereafter in an anaerobic environment using feeding strategy with defined xylose media feed at at least 0.08 $h^{-1}$ in cyclus of feed and disrupted feed in a cyclus time range of a few hours, and
    obtaining the sugar fermenting *Saccharomyces cerevisiae* cells with capability to ferment xylose by collecting said cells from the chemostat reactor.

2. A method according to claim 1, wherein the second *Saccharomyces cerevisiae* haploid strain is obtained from the deposited yeast strain Taurus03 with deposit number CBS128138, Taurus04 with deposit number CBS 128139, Taurus07 with deposit number CBS128140, Taurus10 with deposit number CBS128141, said strains having the β-lactamase gene removed, are haploid and are evolutionary engineered.

3. A method according to claim 1, wherein the first strain of *Saccharomyces cerevisiae* for providing at least 20 tetrads of said strain is *Saccharomyces cerevisiae* USM21 CBS102678.

4. A method according to claim 1, wherein the xylose and geneticin agar plates comprises 50-150 µg/ml geneticin and 15-25 g/L xylose.

5. A method according to claim 1, wherein the minimal defined xylose liquid media used in growing the mated cells is 15-25 g/L xylose defined media liquid culture.

6. A method according to claim 1, wherein sporulating the first strain of *Saccharomyces cerevisiae* proceeds for at least 1 week at at least room temperature, and mating the first sporulated *Saccharomyces cerevisiae* strain with the second *Saccharomyces cerevisiae* haploid strain by mixing proceeds for at least 1 week at at least room temperature.

7. A method according to claim 1, wherein the concentration of mated cells with basic morphology features is in the range of $1\times10^6$ cells/ml-$1\times10^8$ cells/ml.

* * * * *